United States Patent
Chakraborty et al.

(10) Patent No.: US 10,465,105 B2
(45) Date of Patent: Nov. 5, 2019

(54) IN-SITU HYDROGEN SULFIDE MITIGATION

(71) Applicants: Soma Chakraborty, Houston, TX (US); Prasad Dhulipala, Katy, TX (US); Jeffrey Russek, Pearland, TX (US); Sunder Ramachandran, Sugar Land, TX (US); Jack Lynn, Magnolia, TX (US)

(72) Inventors: Soma Chakraborty, Houston, TX (US); Prasad Dhulipala, Katy, TX (US); Jeffrey Russek, Pearland, TX (US); Sunder Ramachandran, Sugar Land, TX (US); Jack Lynn, Magnolia, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 0 days.

(21) Appl. No.: 15/948,243

(22) Filed: Apr. 9, 2018

(65) Prior Publication Data

US 2019/0309213 A1  Oct. 10, 2019

(51) Int. Cl.
| | |
|---|---|
| *C09K 8/54* | (2006.01) |
| *E21B 43/38* | (2006.01) |
| *C12N 9/00* | (2006.01) |
| *C09K 8/90* | (2006.01) |
| *C09K 8/04* | (2006.01) |
| *C12N 9/10* | (2006.01) |
| *C12N 9/02* | (2006.01) |

(52) U.S. Cl.
CPC ............... *C09K 8/54* (2013.01); *C09K 8/04* (2013.01); *C09K 8/905* (2013.01); *C12N 9/0051* (2013.01); *C12N 9/1085* (2013.01); *C12Y 108/05004* (2013.01); *C12Y 205/01047* (2013.01); *E21B 43/38* (2013.01); *C09K 2208/20* (2013.01)

(58) Field of Classification Search
None
See application file for complete search history.

(56) References Cited

U.S. PATENT DOCUMENTS

| | | | | |
|---|---|---|---|---|
| 6,461,859 | B1 * | 10/2002 | Duhalt ........... | C10G 27/12 435/282 |
| 7,101,410 | B1 * | 9/2006 | Baugh ............ | C10G 32/00 435/281 |
| 2004/0002075 | A1 * | 1/2004 | Ishikawa ........ | C12N 9/88 435/6.14 |
| 2016/0039697 | A1 * | 2/2016 | Dhulipala ...... | C12N 9/0051 435/266 |
| 2016/0160105 | A1 * | 6/2016 | Dhulipala ...... | C09K 8/035 166/305.1 |
| 2016/0333307 | A1 * | 11/2016 | Fong .............. | C10L 3/102 |
| 2017/0137790 | A1 * | 5/2017 | Dhulipala ...... | C09K 8/035 |

OTHER PUBLICATIONS

Chaplin, M.; Enzyme Technology; Aug. 6, 2014; pp. 1-2; http://www1.lsbu.ac.uk/water/enztech/ (Year: 2014).*

* cited by examiner

*Primary Examiner* — Anuradha Ahuja
(74) *Attorney, Agent, or Firm* — Cantor Colburn LLP

(57) ABSTRACT

A method of reducing an amount of a sulfur-containing compound in a reservoir fluid includes contacting a treatment fluid comprising an aqueous medium and an enzymatic scavenger with a precipitating fluid to precipitate the enzymatic scavenger; contacting the precipitated enzymatic scavenger with the reservoir fluid comprising the sulfur-containing compound; and reducing a number of the sulfur-containing compound in the reservoir fluid.

19 Claims, No Drawings

Specification includes a Sequence Listing.

IN-SITU HYDROGEN SULFIDE MITIGATION

BACKGROUND

Hydrogen sulfide is a colorless gas with an offensive odor. It is soluble in water and oils. Hydrogen sulfide is often encountered in the oil and gas industry. It can occur naturally as a component of formation gases. Thermal degradation of organic materials and sulfate reducing bacteria (SRB) can also produce hydrogen sulfide. Removal of hydrogen sulfide is warranted because hydrogen sulfide is corrosive, toxic, and flammable.

The process of removing hydrogen sulfide in the oil and gas industry is known as gas sweetening and can be accomplished by either iron sponge $H_2S$ scrubbers or chemical scavengers. Typical hydrogen sulfide scavengers used in the oilfield include amine based scavengers such as triazines, oxidants such as chlorine dioxide, amine-aldehyde condensates, metal carboxylates and chelates.

Recently, certain enzymes have been disclosed as efficient biomolecules that mitigate S-based species, such as hydrogen sulfide and mercaptans. For downhole applications, these biomolecules may be injected in a fluid system containing a carrier. Due to the promising use of the enzymes as non-toxic and environmentally friendly hydrogen sulfide scavengers, alternative methods of delivering the enzymes are needed in the art.

BRIEF DESCRIPTION

A method of reducing an amount of a sulfur-containing compound in a reservoir fluid is disclosed. The method comprises contacting a treatment fluid comprising an aqueous medium and an enzymatic scavenger with a precipitating fluid to precipitate the enzymatic scavenger; contacting the precipitated enzymatic scavenger with the reservoir fluid comprising the sulfur-containing compound; and reducing a number of the sulfur-containing compound in the reservoir fluid.

DETAILED DESCRIPTION

Methods are provided for delivering enzymatic scavengers in an aqueous medium to a desired location such as a subterranean formation, and then precipitating the enzymatic scavengers with a precipitating fluid. Advantageously, the precipitated enzymatic scavengers can be deposited on a surface of the subterranean formation, for example, reservoir rocks. The precipitated enzymatic scavengers can be used continuously to mitigate hydrogen sulfide in a production fluid produced from the subterranean formation as the production fluid flows to a wellbore. By eliminating hydrogen sulfides while production fluids are produced, a safer operation of the well is achieved. In addition, the methods allow for the use of less expensive completion materials in well design and can enhance the lifetime of equipment and tools in a downhole environment.

A method of reducing an amount of a sulfur-containing compound includes contacting a treatment fluid comprising an aqueous medium and an enzymatic scavenger with a precipitating fluid to precipitate the enzymatic scavenger; contacting the precipitated enzymatic scavenger with the reservoir fluid comprising the sulfur-containing compound; and reducing a number of the sulfur-containing compound in the reservoir fluid.

The treatment fluids can be but not necessarily applied downhole. If applied downhole, the treatment fluids are conveyed into a subterranean formation. The methods of conveying include pumping for example at a pressure that is less than the formation fracturing pressure. The pumping can squeeze the treatment fluids into the subterranean formation.

After the treatment fluids are conveyed, the precipitating fluids are delivered to the treatments fluids and come into contact with the treatment fluids. The method of delivering the precipitating fluids include pumping, injecting, or the like. It is appreciated that the treatment fluids and the precipitating fluids can be pumped downhole simultaneously, or the precipitating fluids are conveyed to the subterranean formation first followed by the treatment fluids.

Once the precipitating fluids come into contact with the treatment fluids, enzymatic scavenger precipitates out from the treatment fluids. The precipitated enzymatic scavenger can be in the form of a solid such as solid particles and deposit on a surface of the subterranean formation by absorption, adsorption, or the like.

Additional steps may be included in the method. For example in an embodiment, after introducing the treatment fluids and the precipitating fluids into the subterranean formation, the well is shut-in for a period of time to allow the precipitated enzymatic scavenger to absorb or adsorb onto the surfaces of the formation before producing additional production fluids. During this time the well is closed off so that nothing is introduced into the well or produced from the well. Exemplary shut-in times include a few hours such as 1 to 24 hours.

The precipitated enzymatic scavengers are effective to mitigate sulfur-containing compounds in various reservoir fluids. Such fluids include liquefied petroleum gas, crude oil and petroleum residual fuel, heating oil, a drilling fluid, a servicing fluid, a production fluid, a completion fluid, a rejection fluid, a refinery fluid, wastewater, or a combination comprising at least one of the foregoing. Thus, the methods as disclosed herein are useful in controlling sulfur-containing compounds in water systems, oil and gas production and storage systems, and other similar systems.

As used herein, a sulfur-containing compound includes a sulfide such as $H_2S$, a bisulfide, an organic compound that contains sulfur, or a combination comprising at least one of the foregoing. In an embodiment, the untreated reservoir fluid contains about 1 ppm to about 9,000 ppm, about 5 ppm to about 8,000 ppm, about 10 ppm to about 7,000 ppm, about 50 ppm to about 7,000 ppm, or about 100 ppm to about 7,000 ppm of the sulfur containing compound.

In an embodiment, the reservoir fluid is a production fluid produced from the subterranean formation. The method further comprises flowing the production fluid from the subterranean formation into a wellbore. The production fluid contacts the precipitated enzymatic scavenger as the production fluid flows from the subterranean formation into the wellbore to reduce a number of the sulfur-containing compound in the production fluid.

The precipitating fluids comprise a salt which is ammonium sulfate, potassium chloride, zinc bromide, or a combination comprising at least one of the foregoing. The salt can be present in an amount of about 10 wt. % to about 60 wt. %, about 20 wt. % to about 30 wt. % or about 40 wt. % to about 60 wt. %, based on a total weight of the precipitating fluids. The precipitating fluids can further comprise water. Preferably, the salt is dissolved in the water. In a specific exemplary embodiment, the precipitating fluid is an aqueous solution of about 10 wt. % to about 60 wt. %, about 20 wt. % to about 30 wt. %, about 30 wt. % to about 60 wt.

%, or about 40 wt. % to about 60 wt. % of ammonium sulfate based on a total weight of the precipitating fluid.

Alternatively or in addition, the precipitating fluids comprise an organic solvent which is an alcohol such as a $C_{1-5}$ alcohol, glycerol, or a combination comprising at least one of the foregoing. Methanol, ethanol, and glycerol are specifically mentioned. In an embodiment, the precipitating fluids comprise about 10 to about 60 volume percent, about 20 to about 30 volume percent or about 40 to about 60 volume percent of methanol based on a total volume of the precipitating fluids.

The treatment fluids contain an aqueous medium and an enzymatic scavenger. Additives such as a scale inhibitor, an asphaltene inhibitor, a biocide, or a combination thereof can be included if needed.

The aqueous medium may be a brine, sea water, or fresh water. Suitable aqueous medium include or may be used in combination with fluids have gelling agents, cross-linking agents, gel breakers, surfactants, foaming agents, demulsifiers, buffers, clay stabilizers, acids, or mixtures thereof.

The enzymatic scavenger is present in an amount of about 0.05 ppm to 10,000 ppm or about 0.05 ppm to 5,000 ppm based on the total weight of the treatment fluids. The enzymatic scavengers are disclosed in U.S. Pat. No. 9,587, 159 and U.S. 2016/0039697, the disclosure of both of which is incorporated herein by reference in its entirety.

The enzymatic scavenger comprises a cysteine synthase enzyme, a sulfide quinone reductase enzyme, or a combination comprising at least one of the foregoing; wherein the cysteine synthase enzyme is at least 75%, at least 80%, at least 90%, or at least 95% homologous to the cDNA sequence of SEQ ID NO:1, and the sulfide quinone reductase is at least 75%, at least 80%, at least 90%, or at least 95% homologous to the cDNA sequence of SEQ ID NO:2. cDNA is defined as DNA synthesized from a messenger RNA (mRNA) template in an enzymatic catalyzed reaction using reverse transcriptase.

'Cysteine synthase enzyme' is defined herein to be the active site of the cysteine synthase enzyme to convert a sulfur-containing compound such as hydrogen sulfide into L-cysteine and acetate. The active site may be or include the whole protein, an active fragment of the protein, a mimetic of the protein, and combinations thereof 'Fragment' as used herein is meant to include any amino acid sequence shorter than the full-length cysteine synthase enzyme, but where the fragment maintains similar activity to the full-length cysteine synthase enzyme. Fragments may include a single contiguous sequence identical to a portion of the cysteine synthase enzyme sequence. Alternatively, the fragment may have or include several different shorter segments where each segment is identical in amino acid sequence to a different portion of the amino acid sequence of the cysteine synthase enzyme, but linked via amino acids differing in sequence from the cysteine synthase enzyme. 'Mimetic' as used herein may include polypeptides, which may be recombinant, and peptidomimetics, as well as small organic molecules, which exhibit similar or enhanced catalytic activity as compared to the cysteine synthase enzyme described herein.

The gene for the cysteine synthase enzyme may be codon optimized to increase the efficiency of its expression in *E. coli* or yeast. The nucleotide sequence of one embodiment of the cysteine synthase enzyme is set forth in SEQ ID NO:1. The gene coding for the cysteine synthase enzyme may have a nucleotide sequence that is substantially homologous to the nucleotide sequence of SEQ ID NO:1. The term "substantially homologous" is used herein to denote nucleotides having at least 75% sequence identity to the sequence shown in SEQ ID NO:1, alternatively from about 80% independently to about 99.5%, or from about 85% independently to about 95%.

The sulfide quinone reductase (SQR) enzyme used as a enzymatic scavenger in the treatment fluids may originate from various organisms. The SQR enzyme prevents the formation of sulfur-containing compounds such as hydrogen sulfide. In a preferred embodiment, the nucleotide sequence encoding the SQR enzyme may be derived from a gram negative, acidophilic and thermophilic bacterium, such as *Acidithiobacillus ferroxidans, Metallospora cuprina* and *Metallospora sedula*, using polymerase chain reaction (PCR) amplification. A sulfide quinone reductase DNA sequence from *Acidithiobacillus ferroxidans* is set forth in SEQ ID NO:2. The gene coding for the sulfide quinone reductase enzyme may have a nucleotide sequence that is substantially homologous to the nucleotide sequence of SEQ ID NO:2. The term "substantially homologous" is used herein to denote nucleotides having at least 75% sequence identity to the sequence shown in SEQ ID NO:2, alternatively from about 80% independently to about 99.5%, or from about 85% independently to about 95%. The SQR gene sequence was amplified using *A. ferroxidans* genomic DNA and was cloned in a protein expression vector. A homology may be similar for other SQR enzymes depending on originating organisms.

The treatment fluids can further comprise a pyridoxal phosphate, 0-acetylserine, dithothreitol, coenzyme Q10, plastoquinone, vitamin K2, or a combination comprising at least one of the foregoing.

Set forth are various embodiments of the disclosure.

Embodiment 1

A method of reducing an amount of a sulfur-containing compound in a reservoir fluid, the method comprising: contacting a treatment fluid comprising an aqueous medium and an enzymatic scavenger with a precipitating fluid to precipitate the enzymatic scavenger; contacting the precipitated enzymatic scavenger with the reservoir fluid comprising the sulfur-containing compound; and reducing a number of the sulfur-containing compound in the reservoir fluid.

Embodiment 2

The method as in any prior embodiment, further comprising conveying the treatment fluid and the precipitating fluid into a subterranean formation.

Embodiment 3

The method as in any prior embodiment, wherein the precipitated enzymatic scavenger is deposited on a surface of the subterranean formation.

Embodiment 4

The method as in any prior embodiment, further comprising applying a shut-in period after the treatment fluid and the precipitating fluid are conveyed into the subterranean formation.

Embodiment 5

The method as in any prior embodiment, wherein the reservoir fluid is a liquefied petroleum gas, a crude oil, a petroleum residual fuel, a heating oil, a drilling fluid, a servicing fluid, a production fluid, a completion fluid, a rejection fluid, a refinery fluid, wastewater, or a combination comprising at least one of the foregoing.

Embodiment 6

The method as in any prior embodiment, wherein the reservoir fluid is a production fluid produced from the subterranean formation.

Embodiment 7

The method as in any prior embodiment, further comprising flowing the production fluid from the subterranean formation into a wellbore.

Embodiment 8

The method as in any prior embodiment, wherein production fluid contacts the precipitated enzymatic scavenger as the production fluid flows from the subterranean formation into the wellbore to reduce an amount of the sulfur-containing compound in the production fluid.

Embodiment 9

The method as in any prior embodiment, wherein the precipitating fluid comprises a salt which is ammonium sulfate, potassium chloride, zinc bromide, or a combination comprising at least one of the foregoing.

Embodiment 10

The method as in any prior embodiment, wherein the precipitating fluid further comprises water, and the salt is dissolved in the water.

Embodiment 11

The method as in any prior embodiment, wherein the salt is present in an amount of about 10 wt % to about 60 wt %, based on a total weight of the precipitating fluid.

Embodiment 12

The method as in any prior embodiment, wherein the precipitating fluid is an aqueous solution of about 10 to about 60 wt. % of ammonium sulfate based on a total weight of the precipitating fluid.

Embodiment 13

The method as in any prior embodiment, wherein the precipitating fluid comprises an organic solvent which is an alcohol.

Embodiment 14

The method as in any prior embodiment, wherein the organic solvent is a $C_{1-5}$ alcohol, glycerol, or a combination comprising at least one of the foregoing.

Embodiment 15

The method as in any prior embodiment, wherein the precipitating fluid comprises about 10 to about 60 volume percent of methanol based on a total volume of the precipitating fluid.

Embodiment 16

The method as in any prior embodiment, wherein the enzymatic scavenger is present in an amount of about 0.05 ppm to 10,000 ppm based on the total weight of the treatment fluid.

Embodiment 17

The method as in any prior embodiment, wherein the enzymatic scavenger comprises a cysteine synthase enzyme, a sulfide quinone reductase enzyme, or a combination comprising at least one of the foregoing; the cysteine synthase enzyme is at least 75% homologous to the cDNA sequence of SEQ ID NO:1, and the sulfide quinone reductase is at least 75% homologous to the cDNA sequence of SEQ ID NO:2.

Embodiment 18

The method as in any prior embodiment, wherein the treatment fluid further comprises one or more of the following: a pyridoxal phosphate; 0-acetylserine; dithothreitol; coenzyme Q10; plastoquinone; or vitamin K2.

All ranges disclosed herein are inclusive of the endpoints, and the endpoints are independently combinable with each other. As used herein, "combination" is inclusive of blends, mixtures, alloys, reaction products, and the like. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." The modifier "about" used in connection with a quantity is inclusive of the stated value and has the meaning dictated by the context (e.g., it includes the degree of error associated with measurement of the particular quantity).

What is claimed is:

1. A method of reducing an amount of a sulfur-containing compound in a reservoir fluid, the method comprising:
   contacting a treatment fluid comprising an aqueous medium and an enzymatic scavenger with a precipitating fluid to precipitate the enzymatic scavenger in a subterranean formation;
   contacting the precipitated enzymatic scavenger with the reservoir fluid comprising the sulfur-containing compound; and
   reducing the amount of the sulfur-containing compound in the reservoir fluid,
   wherein the precipitating fluid comprises water and a salt dissolved in the water, the salt is ammonium sulfate, potassium chloride, zinc bromide, or a combination comprising at least one of the foregoing; or
   the precipitating fluid comprises an organic solvent which is an alcohol; or
   the precipitating fluid comprises water, the salt, and the organic solvent.

2. The method of claim 1, further comprising conveying the treatment fluid and the precipitating fluid into the subterranean formation.

3. The method of claim 2, wherein the precipitated enzymatic scavenger is deposited on a surface of the subterranean formation.

4. The method of claim 2, further comprising applying a shut-in period after the treatment fluid and the precipitating fluid are conveyed into the subterranean formation.

5. The method of claim 2, wherein the reservoir fluid is a production fluid produced from the subterranean formation.

6. The method of claim 5, further comprising flowing the production fluid from the subterranean formation into a wellbore.

7. The method of claim 6, wherein the production fluid contacts the precipitated enzymatic scavenger as the production fluid flows from the subterranean formation into the wellbore to reduce an amount of the sulfur-containing compound in the production fluid.

8. The method of claim 1, wherein the reservoir fluid is a liquefied petroleum gas, a crude oil, a petroleum residual fuel, a heating oil, a drilling fluid, a servicing fluid, a production fluid, a completion fluid, a refinery fluid, wastewater, or a combination comprising at least one of the foregoing.

9. The method of claim 1, wherein the precipitating fluid comprises water and the salt.

10. The method of claim 9, wherein the salt is present in an amount of about 10 wt % to about 60 wt %, based on a total weight of the precipitating fluid.

11. The method of claim 1, wherein the precipitating fluid comprises water and the salt, wherein the salt is ammonium sulfate, and the ammonium sulfate is present at about 10 to about 60 wt. % based on a total weight of the precipitating fluid.

12. The method of claim 1, wherein the precipitating fluid comprises the organic solvent.

13. The method of claim 12, wherein the organic solvent is a $C_{1-5}$ alcohol, glycerol, or a combination comprising at least one of the foregoing.

14. The method of claim 12, wherein the organic solvent is methanol and the precipitating fluid comprises about 10 to about 60 volume percent of the methanol based on a total volume of the precipitating fluid.

15. The method of claim 1, wherein the enzymatic scavenger is present in an amount of about 0.05 ppm to 10,000 ppm based on the total weight of the treatment fluid.

16. The method of claim 1, wherein the enzymatic scavenger comprises a cysteine synthase enzyme, a sulfide quinone reductase enzyme, or a combination comprising at least one of the foregoing; the cysteine synthase enzyme is at least 75% homologous to the cDNA sequence of SEQ ID NO:1, and the sulfide quinone reductase is at least 75% homologous to the cDNA sequence of SEQ ID NO:2.

17. The method of claim 1, wherein the treatment fluid further comprises one or more of the following: a pyridoxal phosphate; O-acetylserine; dithothreitol; coenzyme Q10; plastoquinone; or vitamin K2.

18. The method of claim 1, further comprising conveying the treatment fluid into the subterranean formation; and conveying the precipitating fluid into the subterranean formation subsequent to conveying the treatment fluid.

19. The method of claim 1, further comprising pumping the treatment fluid at a pressure that is less than a formation fracturing pressure to squeeze the treatment fluid into the subterranean formation; and
   conveying the precipitating fluid into the subterranean formation subsequent to conveying the treatment fluid.

* * * * *

SEQUENCE LISTING

<160> NUMBER OF SEQ ID NOS: 2

<210> SEQ ID NO 1
<211> LENGTH: 1197
<212> TYPE: DNA
<213> ORGANISM: Aeropyrum pernix

```
<400> SEQUENCE: 1
atgagaggat cgcatcacca tcaccatcac gcgctggcgg atattagcgg ctatctggat      60
gtgctggata gcgtgcgcgg ctttagctat ctggaaaacg cgcgcgaagt gctgcgcagc     120
ggcgaagcgc gctgcctggg caacccgcgc agcgaaccgg aatatgtgaa agcgctgtat     180
gtgattggcg cgagccgcat tccggtgggc gatggctgca gccataccct ggaagaactg     240
ggcgtgtttg atattagcgt gccgggcgaa atggtgtttc gagcccgct ggattttttt     300 gaacgcggca aaccgacccc gctggtgcgc agccgcctgc agctgccgaa cggcgtgcgc     360
gtgtggctga aactggaatg gtataacccg tttagcctga gcgtgaaaga tcgcccggcg     420
gtggaaatta ttagccgcct gagccgccgc gtggaaaaag gcagcctggt ggcggatgcg     480
accagcagca actttggcgt ggcgctgagc gcggtggcgc gcctgtatgg ctatcgcgcg     540
cgcgtgtatc tgccgggcgc ggcggaagaa tttggcaaac tgctgccgcg cctgctgggc     600
gcgcaggtga ttgtggatcc ggaagcgccg agcaccgtgc atctgctgcc gcgcgtgatg     660
aaagatagca aaaacgaagg ctttgtgcat gtgaaccagt tttataacga tgcgaacttt     720
gaagcgcata tgcgcggcac cgcgcgcgaa attttgtgc agagccgccg cggcggcctg     780
gcgctgcgcg gcgtggcggg cagcctgggc accagcggcc atatgagcgc ggcggcgttt     840
tatctgcaga gcgtggatcc gagcattcgc gcggtgctgg tgcagccggc cagggcgat      900 agcattccgg gcattcgccg cgtggaaacc ggcatgctgt ggattaacat gctggatatt     960
agctataccc tggcggaagt gaccctggaa gaagcgatgg aagcggtggt ggaagtggcg    1020
cgcagcgatg gcctggtgat tgcccgagc gcggcgcgg cggtgaaagc gctggcgaaa     1080
aaagcggcgg aaggcgatct ggaaccgggc gattatgtgg tggtggtgcc ggataccggc    1140
tttaaatatc tgagcctggt gcagaacgcg ctggaaggcg cgggcgatag cgtgtaa       1197

<210> SEQ ID NO 2
<211> LENGTH: 1128
<212> TYPE: DNA
<213> ORGANISM: Acidithiobacillus ferrooxidans

<400> SEQUENCE: 2
atgacccaag tgaccattat cggcgcaggc tttggtggct tgacggccgt ccgccacctg      60
cgtcgccgga tgcccgacgc ggaaatcacc gtcatcgcac ccaggcgga gttcgtttac      120 taccccagcc tgatctggat tcccaccggg ctgcggcaag gcgagaatct gcggattccc     180
ctggaccgtt tctttcagcg ccgacgagtg cagtttcatc agggtcgcgt cactggcctg     240
cgcgatggcg gccgtaccgt catcaccgac cagggtgaag tgcggaacga cgcgctcatc     300
attgccagcg gcgtcgcgg tattcgtaag ctgccgggca tcgaacacag tttcgccatc     360
tgcgacggta tcgatgccgc cgaaaacatc cgagaccgct ggcgctgat ggacaaaggc     420 accattgcct tcggtttcgc cggcaatccc ctggagccga ccgccgtacg cggtggtccg     480
gtctttgaac tgctctttgg aatcgacact taccttcgtc agatcgataa gcgcgggcaa     540
atcgaattgg tattttttcaa tccgatgacc gaaccgggta tcgactggg tccgaaggcg     600 gtggaaggac tgctcgcgga aatgcagcgg cgcgatattc gcacccatct tggtcataaa     660
atcagtgggt tctcggtaaa caaagtgatg accgaaggcg cgacattgc cgcggacctg     720 atcctgttca tgccggcat gaccggcccg gactgggcag ccgacagcgg tttgccctc      780 tctgccggtg gcttttttca gtccgacctg cactgcaccg tccccgacca tccgggcgtc     840
tttgtcattg gtgacggggg gtcctacgcg ggcagcccgg actggctacc caagcagggc    900
```

```
cacatggcgg  acctgcaggc  cgggaccgcc  gtgcataacc  tgctcctgca  tctgcagggg        960
aaggcggcag  acaataccct  ccgcagcgag  ttgatctgca  ttgtcgacac  cttggacagc       1020
ggcatcatgg  tctatcgcag  ccccaatcat  gccagcatcc  tgccaaactc  gctctggcat       1080
gcggccaagg  tcgcctttga  gtggcgttat  ctgttgcatt  accgctga                     1128
```